United States Patent [19]

Uster et al.

[11] Patent Number: 5,064,655

[45] Date of Patent: * Nov. 12, 1991

[54] LIPOSOME GEL COMPOSITION AND METHOD

[75] Inventors: Paul S. Uster, Palo Alto; Jacqueline K. Morano, Montain View; Francis J. Martin, San Francisco, all of Calif.

[73] Assignee: Liposome Technology, Inc., Menlo Park, Calif.

[*] Notice: The portion of the term of this patent subsequent to Jul. 31, 2007 has been disclaimed.

[21] Appl. No.: 356,262

[22] Filed: May 23, 1989

Related U.S. Application Data

[63] Continuation-in-part of Ser. No. 315,392, Feb. 23, 1989, Pat. No. 4,944,948.

[51] Int. Cl.$^5$ .............................................. A61K 37/22
[52] U.S. Cl. .................................... 424/450; 424/1.1; 264/4.3; 428/402.2
[58] Field of Search .................... 424/450, 1.1; 264/4.3

[56] References Cited

U.S. PATENT DOCUMENTS 4,781,871 11/1988 West, III et al. ................ 424/450 X
4,944,948 7/1990 Uster et al. ............................ 424/450

FOREIGN PATENT DOCUMENTS

WO88/00824 2/1988 PCT Int'l Appl. .

OTHER PUBLICATIONS

Brown, G. L., et al., Ann. Surg. 208(6):788 (1988).
Kato, M., et al., Biochem. Biophys. Res. Comm. 129(2):373 (1985).
Fujii, D. K., et al., J. Cell Physiol. 114:267 (1983).
Bettger, W. J., et al., Proc. Natl. Acad. Sci. U.S.A. 78(9):5588 (1981).
Franklin, T., et al., J. Lab. Clin. Med. 108(2):103 (1986).
Buckley, A., et al., Proc. Natl. Acad. Sci. U.S.A. 82:7340 (1985).
Buckley, A., et al., J. Surg. Res. 43:322 (1987).
Mayhew, E., et al., Exp. Cell. Res. 171:195 (1987).

Primary Examiner—Thurman K. Page
Assistant Examiner—Donald R. McPhail
Attorney, Agent, or Firm—Peter J. Dehlinger

[57] ABSTRACT

A liposome gel composition and method of preparing the same. The composition is composed of charged liposomes, at a relatively low lipid concentration, in a low-conductivity medium. The composition preferably contains a zwitterionic compound at its isoelectric point. The liposomes can be designed for cosmetic use, transdermal drug delivery, or enhanced retention on mucosal tissues, such as for ophthalmic use.

33 Claims, 1 Drawing Sheet

LIPOSOME GEL COMPOSITION AND METHOD

The present invention is a continuation-in-part application of U.S. patent application for "EGF/Liposome Gel Composition and Method", Ser. No. 315,392, filed Feb. 23, 1989 now U.S. Pat. No. 4,944,948.

1. Field of the Invention

The present invention relates to a high-viscosity liposome gel composition, and to methods of making and using the composition.

2. References

Mayhew, E., et al., Exp. Cell Res, 171:195 (1987). Mezei, M., et al., Life Sciences, 26:1473 (1980). Mezei, M., et al., J Pharm Pharmacol, 34:473 (1981). Szoka, F., et al., Proc Nat Acad Sci, US, 75:4194 (1978). Szoka, F., et al., Ann Rev Biophys Bioeng, 9:467 (1980).

3. Background of the Invention

Lipid bilayer vesicles, or liposomes, have been proposed for use in a variety of topical applications. In the cosmetics industry, liposome formulations are currently sold as a lipid supplement to enhance dry or aging skin. Liposomes may also be useful for applying compounds, such as ultraviolet-blocking agents, vitamin A, retinoic acid and other retinoids, and the like to the skin, to achieve greater drug solubility or skin compatibility, reduced irritation from the drug, and/or extended drug release.

Liposomes also offer the potential of improved transdermal drug delivery. It is known, for example, that liposomes are able to facilitate the uptake of certain lipophilic compounds, such as anti-inflammatory steroid compounds, across the skin barrier (Mezei, 1980, 1981), and the drug-uptake characteristics of the liposomes can be modulated by varying lipid composition in the liposomes. Additionally, the liposomes can be formulated with coentrapped agents, such as azacycloalkan-2-ones, which facilitate transdermal uptake of drugs (U.S. Pat. No. 4,316,893), to improve and/or modulate transdermal drug release characteristics.

The properties of liposomes also make them desirable for use in wound-healing. Co-pending patent application for "EGF/Liposome Gel Composition and Method", for example, describes a liposome formulation of epidermal growth factor (EGF) designed for application to wound sites, such as a surgical wound site, to provide sustained release of EGF at the site.

Liposomes are also promising drug-delivery vehicles for sustained drug release on mucosal surfaces, including corneal tissue. In ophthalmic use, for example, liposomes can provide delayed drug release, and greater solubility of lipid-soluble drugs, for release at the corneal surface, and liposomes alone are useful as a lipid supplement for dry eye (U.S. Pat. No. 4,818,537). Additionally, liposomes can be engineered for enhanced retention on mucosal surfaces, to extend the period of effective drug delivery with each liposome application (U.S. Pat. No. 4,804,539).

In all of the above topical uses of liposomes, it is generally desirable to administer the liposome preparation in a viscous form. In particular, the ideal liposome preparation is a gel which is preferably sufficiently viscous to give persistance at the site of application, especially at a wound site or mucosal tissue site. In cosmetic applications, the gel material should be clear or translucent and preferably be non-greasy to the touch.

Heretofore, viscous liposome pastes have been prepared by forming liposomes at high lipid concentrations--for example, by concentrating conventional, dilute liposome preparations. The high lipid concentrations make these formulations relatively expensive in terms of materials cost. The viscosity of the paste material may also complicate processing steps used, for example, to sterilize the liposomes or remove nonentrapped drug molecules. Further, liposome paste preparations are somewhat greasy to the touch.

Liposome gel formulations have been produced heretofore by suspending liposomes in gel-forming colloidal materials, such as Hydrogel TM, collagen, synthetic polymers, and the like. Although liposome-in-gel formulations of this type can be prepared with desired physical properties, the gel-forming matrix itself may be toxic or otherwise incompatible with the site of application, and may leave a residue at the site of application.

4. Summary of the Invention

It is therefore one object of the invention to provide a high-viscosity liposome gel composition which provides many of the above-discussed desired features of a viscous liposome formulation for topical use.

The invention includes, in one aspect, a high-viscosity liposome gel composition for use in topical application to the skin, in skin wounds, and on mucosal tissue. The composition includes a suspension of charged liposomes in a low-conductivity aqueous suspension medium which has a selected pH between 3.5 and 10.5 and preferably between about 5.5 and 8.5. The liposomes contain at least about 5 weight percent charged vesicle-forming lipids, and the balance of neutral vesicle-forming lipids. The concentration of lipids in the composition is between about 7-25 weight percent and preferably between about 8-15 weight percent.

The aqueous suspension preferably contains a zwitterionic compound, such as a neutral amino acid, whose isoelectric point is at the selected pH of the composition.

In one general embodiment, the charged vesicle-forming lipids are negatively charged phospholipids, such as phosphatidylglycerol (PG). One preferred liposome composition includes approximately equal weight proportions of PG, phosphatidylcholine (PC), and cholesterol.

In another general embodiment, for use in administering a drug to mucosal tissue, the charged vesicle-forming lipids are positively charged lipid components, such as a phosphatidylethanolamine (PE) conjugate prepared by derivatizing PE with a basic amino acid, or a benzylamine lipid, such as benzyldimethylstearylammonium chloride (BDSA).

The invention also includes a high-viscosity liposome gel composition formed of a suspension of charged liposomes in a low-conductivity aqueous suspension medium. According to an important aspect of the composition, the aqueous medium has a selected pH between 3.5 and 10.5, and preferably between about 5.5 and 8.5, and contains a zwitterionic compound, such as an amino acid, whose isoelectric point is within the pH specified range. The zwitterionic compound allows the viscosity of the composition to be selectively varied by adjusting the pH of the medium.

The invention further includes a composition for use in administering liposome lipids or a liposome-entrapped drug to mucosal tissue. The composition is formed of positively charged liposomes in a low-conductivity aqueous suspension medium which has a selected pH between about 3.5 and 10.5. The charged lipids preferably contain a spacer for spacing the positively charged moiety of the lipid away from the lipid bilayer region of the liposomes.

The liposome gel composition is formed, according to the method of the invention, by adding a mixture of vesicle-forming lipids containing at least about 5 weight percent vesicle-forming lipids which are charged at a selected pH between 3.5 and 10.5, and preferably about 5.5 and 8.5, with a low-conductivity aqueous suspension medium, at a final total lipid concentration of between about 7–25 weight percent.

The lipids may be added directly to a low-conductivity aqueous medium or, alternatively, may be added to an aqueous medium containing a zwitterionic compound whose isoelectric point is substantially different from that of the pH of the medium (such that the medium has relatively high conductivity). Following formation of a fluidic liposome suspension, the medium is titrated to a pH at which the zwitterionic compound is at its isoelectric point, yielding a low-conductivity condition which results in gel formation in the suspension. The liposome suspension may be more easily sized, freed of non-liposome-bound drug, filter-sterilized or otherwise processed in the more fluidic state prior to gelling.

These and other objects and features of the invention will become more fully apparent when the following detailed description of the invention is read in conjunction with the accompanying drawings.

DETAILED DESCRIPTION OF THE INVENTION

I. Liposome Gel Compositions

A. Definitions

Figure 1:
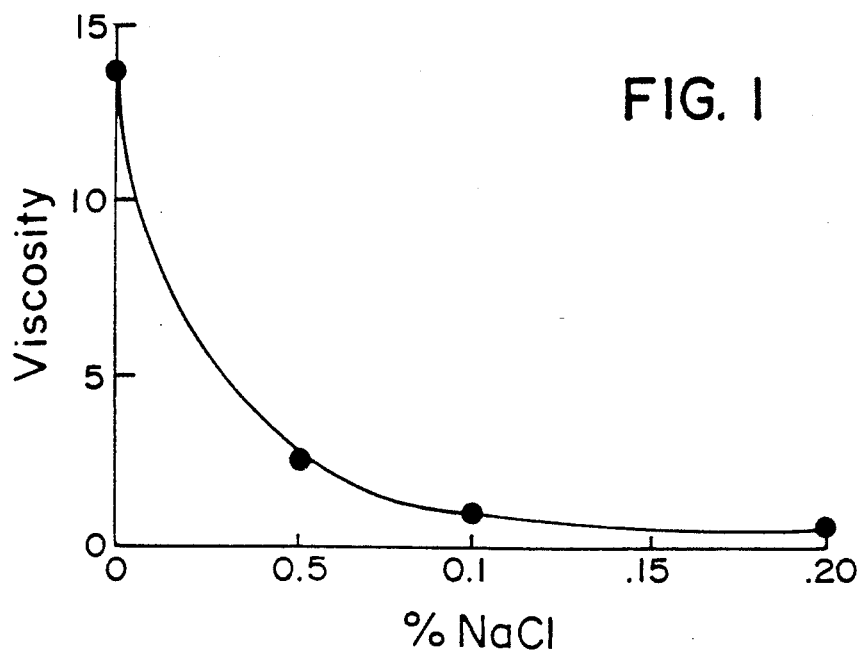
FIG. 1 is a plot of viscosity of a liposome suspension formed in accordance with the present invention, as a function of concentration of univalent electrolyte.

As used herein, the terms below have the following meaning:

1. "Neutral vesicle-forming lipids" refers to any amphiphathic lipid or lipid mixture (i) capable of forming stable lipid bilayer vesicles in the presence of charged vesicle-forming lipids, at a selected concentration of charged lipids between 5–50 weight percent of total lipids, and (ii) having a polar head group with no net charge at a selected pH between 3.5–10.5, and preferably between about 5.5 and 8.5.

2. "Charged vesicle-forming lipids" refers to any amphipathic lipid or lipid mixture (i) capable, at a selected concentration of at least about 5 weight percent, of forming stable lipid bilayers in the presence of neutral vesicle-forming lipids, and (ii) having a polar head group with a net negative or positive charge at a pH between about 3.5–10.5, and preferably between 5.5 and 8.5.

3. "Cholesterol" refers to cholesterol and related unchanged cholesterol analogues and derivatives.

4. "Gel" or "gel-like" refers to a viscous, relatively non-flowable gel state.

5. A "low-conductivity aqueous medium" refers to an aqueous medium whose conductivity is no more than that of a fully ionized univalent electrolyte whose concentration is between about 5–10 mM. Preferably, the low-conductivity medium is one which reduces the Debye length of a charged liposome by no more than half its value at a concentration of fully ionized univalent electrolyte of about 1 mM.

B. Lipid Components

The liposome gel composition formed in accordance with the invention is prepared to contain at least about 5 weight percent charged vesicle-forming lipids which impart a net negative or net positive charge to the liposome surfaces of neutral vesicle-forming lipids.

Preferred neutral vesicle-forming lipids are phospholipids such as phosphatidylcholine (PC), sphingomyelin, and cholesterol. Neutral phospholipids lipids having a variety of acyl chain groups of varying chain length and degree of saturation are available, or may be isolated or synthesized by well-known techniques. In general, partially unsaturated phosphatidylcholine (PC), such as egg PC (EPC) or soy PC (SPC), or fully or partially hydrogenated egg PC (HEPC) or soy PC (HSPC) are readily obtained and provide suitable liposome characteristics, such as ease of extrusion and stability.

Cholesterol and related uncharged neutral analogues thereof, such as 5,6,-cholestene and cholestane, are typically present at about 10–50 weight percent. Cholesterol is known to increase the stability of liposomes and, in the case where the phospholipid components are relatively unsaturated, to increase the packing density of the lipids in the liposomal bilayers. One advantage of cholesterol, where the liposomes are applied at a wound or surgical site, is potentially reduced toxicity due to lipid exchange between the liposomes and cells at the wound or surgical site. It has been demonstrated, for example, with several cultured tumor cell lines, that liposomes containing entrapped epidermal growth factor (EGP) inhibit cellular growth in vitro, and that for at least some cell lines, this inhibition can be greatly reduced by the addition of cholesterol to EPC liposomes (Mayhew).

Preferred negatively charged vesicle-forming lipids include negatively charged phospholipids, such as phosphatidylglycerol (PG), phosphatidylserine (PS), and phosphatidylinositol (PI). One preferred negatively charged phospholipid is partially or fully saturated saturated PG, such as egg PG (EPG). Alternatively, or in addition, the charged components may include charged cholesterol derivatives such as cholesterol sulfate and cholesterol hemisuccinate.

One preferred class of positively charged vesicleforming lipids includes positively charged phospholipids, such as phoshatidylethanolamine (PE) or other phospholipids which have been derivatized at their polar head groups with amines to produce a net positive charge. Methods of producing derivatized phospholipids of this type are described in U.S. Pat. No. 4,804,539. By way of example, PE can be derivatized with basic amino acids, such as lysine, to produce vesicle-forming lipids whose positive charge is separated from the phosphate groups of the lipid by a several-atom spacer.

Another general class of positively charged vesicle-forming lipids include benzyl/aliphatic-chain amines which are (a) capable of being anchored in a liposome bilayer by virtue of the aliphatic chain, and (b) carry a net positive charge at a selected pH preferably between about 5.5 and 8.5. The aliphatic chain is at least about 12 carbons in length, and the amine is preferably a quaternary amine whose remaining (two) nitrogen linked groups are short-chain alkyl groups, such as methyl or ethyl groups, as detailed in U.S. Pat. No. 4,818,537. One preferred compound is benzyldimethylstearylammonium chloride (BDSA).

Cholesterol amines form another class of positively-charged vesicle-forming lipids which are suitable for use in the invention. Cholesterol derivatives of the type Ch—O—C—Y—N and Ch—NH—Y—N, where ChOH is cholesterol, Y is a short carbon-containing chain, and N is an amine, have been described in co-owned U.S. Pat. No. 4,804,539.

Finally, the charged lipid component may include a lipophilic drug which tends to be tightly bound to the lipid bilayer phase of the liposomes.

The lipid components forming the liposomes contain at least about 5 weight percent charged lipid component, and preferably between about 20-40 weight percent charged lipid. The balance of the lipids are neutral vesicle-forming lipids. The following lipid compositions, expressed in weight percent, are exemplary:
1. HEPC:EPG, 95:5;
2. EPC:EPG, 80:20;
3. EPC:EPG, 50:50;
4. EPC:EPG:cholesterol, 50:20:30;
5. EPC:EPG:cholesterol, 33:33:33;
6. EPC:cholesterol sulfate, 80:20;
7. EPC:cholesterol:cholesterol sulfate 50:30:20;
8. FSPC:PE 80:20;
9. FSPC:lysinyl PE 80:20;
10. EPC:cholesterol:cholesterol amine 60:20:20;
11. PC:BDSA 90:10; and
12. PC:BDSA 75:25.

It is noted that the total amount of neutral and charged cholesterol together is preferably no more than 50 weight percent. Further, it is understood that the liposome composition may contain a variety of other lipid components which may enhance liposome stability, drug release characteristics, and/or materials cost. For example, the liposomes may include $\alpha$-tocopherol, or a pharmaceutically acceptable analogue thereof, at a total concentration of between about 0.1 to 2 weight percent, to improve lipid stability on storage, or other lipid-protective agents, such as BHT or chelating agents.

C. Low-Conductivity Aqueous Medium

According to an important feature of the invention, it has been discovered that hydration of vesicle-forming lipids having the above composition with a low-conductivity aqueous medium produces a liposome composition which is both gel-like in consistency and viscosity, and has a relatively low lipid concentration.

More specifically, the combination of liposome surface charge, due to the presence of charged lipid component(s) and the low-conductivity aqueous medium produces a liposome composition characterized by (a) a viscous, gel-like consistency and (b) a relatively low lipid concentration, e.g., 70-250 mg/g composition.

The aqueous medium preferably includes a zwitterionic compound whose isoelectric point (at which the compound is effectively a non-electrolyte) is at the selected pH of the medium between 3.5 and 10.5, and preferably between about pH 5.5 and 8.5. Neutral amino acids, such as glycine, isoleucine, alanine, proline, and valine are preferred zwitterionic compounds. The final concentration of zwitterionic compound in the buffer is typically at least about 0.5 percent by weight and preferably between about 1-5 percent by weight, and the buffer is adjusted in pH to the isoelectric point of the compound to achieve the gel state.

As will be discussed in Section D below, the aqueous medium may initially be adjusted to a pH at which the zwitterionic compound is substantially in a charged form, so that the medium has a relatively high electrolyte concentration, i.e., a relatively high conductivity. By adjusting the pH to the isoelectric point of the zwitterionic compound, typically after lipid hydration and liposome formation, the compound becomes non-electrolytic, liposome formation, the compound becomes non-electrolytic, i.e., has the desired low conductivity.

It is noted, however, that the final salt concentration of the medium, after adjusting the pH to the isoelectric point of the zwitterionic compound, must not produce a significant increase in the ionic strength of the medium. This objective can be achieved, for example, by employing volatile ammonium salts, or as described below, by employing an initially low concentration of zwitterionic compound.

Alternatively, or in addition, the aqueous medium may include other non-electrolyte solute compounds, such as sugar, uncharged water-soluble drugs, and the like which produce a desired osmolarity of the final gel composition.

D. Preparing the Gel Composition

The gel composition of the invention is formed by mixing the neutral and charged vesicle-forming lipids described in Section B with the above low-conductivity aqueous medium, at a final lipid concentration of between about 8-25 weight percent lipid, and preferably between about 8-15 weight percent lipid.

In one general embodiment of the method, the lipids are added directly to the low-conductivity medium, such that when the selected final lipid concentration is reached, the suspension assumes a gel-like state at room temperature.

According to one procedure, vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form.

This film is covered with a selected amount of the low-conductivity medium, and allowed to hydrate, typically over a 15-60 minute period with agitation. The size distribution of the resulting multi-lamellar vesicles (MLVs) can be shifted toward smaller sizes by hydrating the lipids under more vigorous agitation conditions. The final concentration of liposomes is at least 70 mg/g and preferably between about 80-150 mg/g composition. The hydration step is generally effective to produce a homogeneously hydrated liposome suspension, where relatively small lipid quantities are involved.

For larger lipid amounts, the hydrated suspension may contain particles of non-hydrated or partially hydrated lipids. This suspension can be converted to a homogeneous suspension by further processing, preferably by extrusion through a defined-pore size membrane, such as a 2 micron pore size polycarbonate membrane. This general procedure for preparing a liposome gel suspension is illustrated in Example 1.

In another procedure, the lipids are added to the low-conductivity medium by injecting the lipids in a lipid-in-solvent solution into the medium, until the desired lipid concentration (gel viscosity) is reached. This method is illustrated in Example 4.

It will be appreciated that water-soluble drugs or agents can be encasulated in the liposomes formed in the gel by dissolving the drug or agent in the hydration medium. Similarly, a lipophilic compound can be conveniently added to the lipid mixture prior to hydration, for preparing liposomes with entrapped lipophilic drug. It is recognized that the drug itself cannot be such as to defeat the charge on the liposomes or the low-conductivity property of the aqueous medium.

In a second general embodiment of the method, the lipids are added to an aqueous medium containing a zwitterionic compound, at a pH which is substantially different from the isoelectric point of the compound. In particular, the concentration of zwitterionic molecules having a net positive or negative charge is such that the aqueous medium has a moderate conductivity, i.e., above that corresponding to a univalent electrolyte concentration of greater than about 10-20 mM. Typically the medium is at least about 20 mM zwitterionic compound having a net positive or negative charge. For example, the medium may be 100 mM zwitterionic compound, at a pH at which 20 percent of the compound has a net charge.

The liposome suspension formed in the aqueous medium is relatively fluidic, i.e., characterized by high flow characteristics. Because of its fluidity, this suspension is easily processed to achieve desired liposome/suspension characteristics. For example, the suspension may be further processed to (a) achieve smaller and or more uniform liposome sizes, (b) remove free water-soluble drug and/or (c) sterile filter the liposome preparation, according to known methods.

After liposome processing, the non-viscous liposome suspension is converted to the desired gel form by titrating the pH of the suspension to a isoelectric point of the zwitterionic species. As mentioned above, the titration must be carried out without significantly increasing the concentration of dissociable salts in the medium. This can be done by titrating with acids or bases which produce volatile salt components, such as certain ammonium salts, or which produce insoluble salts. Preferably, the titration is done by forming an initial liposome suspension in a medium containing low zwitterionic concentration, then titrating with a concentrated solution of the same zwitterionic compound, until the desired pH is reached, as detailed in Example 3.

E. Viscosity of the Gel Composition

The liposome gel composition of the invention is characterized by a high viscosity which is maintained at a low ionic strength, but which collapses as ionic strength is increased. This feature is illustrated in the study described in Example 2. Here liposomes containing equal-weight amounts of EPG, EPC, and cholesterol were prepared in a 2.3% w/v glycine buffer at isoelectric pH (pH 6.0) buffer, as detailed in Example 1.

The mean viscosity for the samples was $13.3 \times 10^3$ Cps (centipoise) at 1.0 per second shear rate, characterized by a thick, relatively non-flowing gel consistency. With addition of NaCl to a concentration of only 0.05% w/v (about 8.5 mM), the material lost its gel-like properties, being quite fluid, with a mean viscosity of only about $2.7 \times 10^3$ Cps at 1 per second. Further decreases in viscosity were seen with further addition of NaCl to a final concentration of 0.2% w/v (about 34 mM). The loss of viscosity at low NaCl concentration is seen in FIG. 1.

Figures 2A, 2B, 2C:
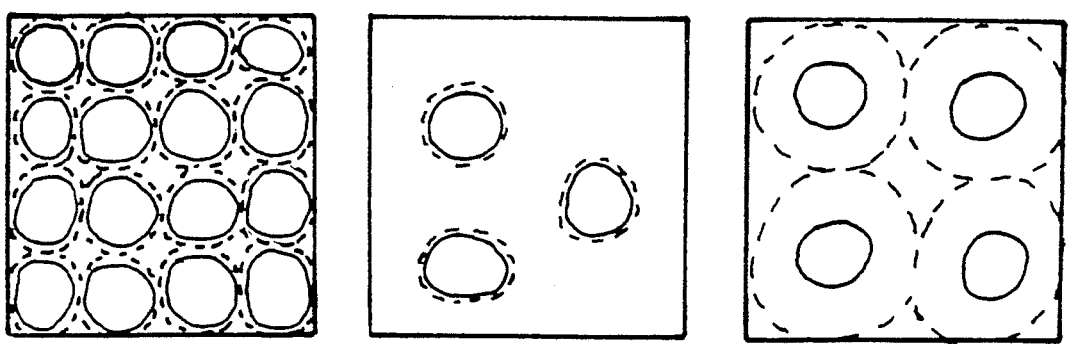
FIGS. 2A–2C are models of liposome packing in a concentrated liposome paste (FIG. 2A) a conventional fluidic dilute liposome suspension (FIG. 2B) and a viscous dilute liposome gel prepared according to the present invention (FIG. 2C).

The nature of the high viscosity gel composition can be appreciated from the liposome suspension models illustrated in FIGS. 2A-2C. The model shown in FIG. 2A represents a liposome paste or concentrate containing a maximum concentration of lipid vesicles in an aqueous suspension medium. Empirically, viscous, paste-like lipid suspensions having a lipid concentrations of up to about 500 μg/ml, at which about 70% of the total aqueous volume is encapsulated, can be produced.

The model of a liposome concentrate shown in FIG. 2A assumes that at high lipid concentrations, and in the absence of surface charge effects, liposomes are able to form close packed suspensions in which the liposomes are densely packed, as indicated, being separated from one another only by a thin shell of ordered water (shown in dotted line). This model, in which the suspension contains relatively little extra liposomal-water, is consistent with the high percent of encapsulated water (up to 70%) observed in high-concentration liposome paste formulations.

FIG. 2B shows a conventional liposome suspension containing about one-fifth the lipid concentration of the FIG. 2A paste, e.g., about 100 μg/ml. Assuming the suspension is composed of the same types of liposomes, more than 80% of the aqoueus medium in the suspension would be non-encapsulated water, and each liposome is now free to move through relatively large aqueous volume elements, as shown. As a result, the suspension has a low viscosity, i.e., is freely flowable.

FIG. 3C shows the same low concentration of liposomes as in FIG. 2B, but in a suspension formed in accordance with the invention in which the liposomes contain at least about 5 weight percent charged lipid component and are suspended in a low-conductivity medium. The low lipid concentration of the suspension indicates that more than 80% of the total volume of the suspension is extra-liposomal water, i.e., non-encapsulated water. However, the high viscosity of the medium indicates that the liposomes are arrayed in packed spheres, as in FIG. 2A.

These two assumptions are consistent with a model in which each liposome is surrounded by a relatively large spherical shell which contains a volume of up to several times that of the liposome, but which itself cannot be readily penetrated by the shells of neighboring liposomes. The thickness of a spherical water shell which is required to produce a "close-packing" arrangement of shells at a selected lipid concentration can be calculated using the following simplying assumptions: (a) the maximum volume of liposome-encapsulated medium (at a lipid concentration of 500 μg/ml, at which the shell thickness is essentially zero) is about 70 percent; (b) in both high-and low-concentration suspensions, the liposomes have uniform sizes of about 2,000 Å; and (c) the total number of liposomes in the suspension which is proportional to lipid concentration. The calculated shell thicknesses are given in Table 1.

TABLE 1

| Lipid Concentration (μg/ml) | Shell Thickness (Å) |
|---|---|
| 100 | 1400 |
| 200 | 700 |
| 300 | 400 |
| 400 | 150 |
| 500 | 0 |

Since the immobilization of the liposomes in the dilute susensions is assumed to be due to charge repulsion among unshielded charged-surface liposomes, the thicknesses of these shells provide a rough estimate of the distance over which the charged liposomes exert an appreciable charge repulsion effect. Thus, in a viscous liposome suspension having a lipid concentration of 100 μg/ml, the charged 2,000 Å liposomes exert a charge repulsion effect over a distance of about 1,400 Å from the liposome surfaces.

Figure 3:
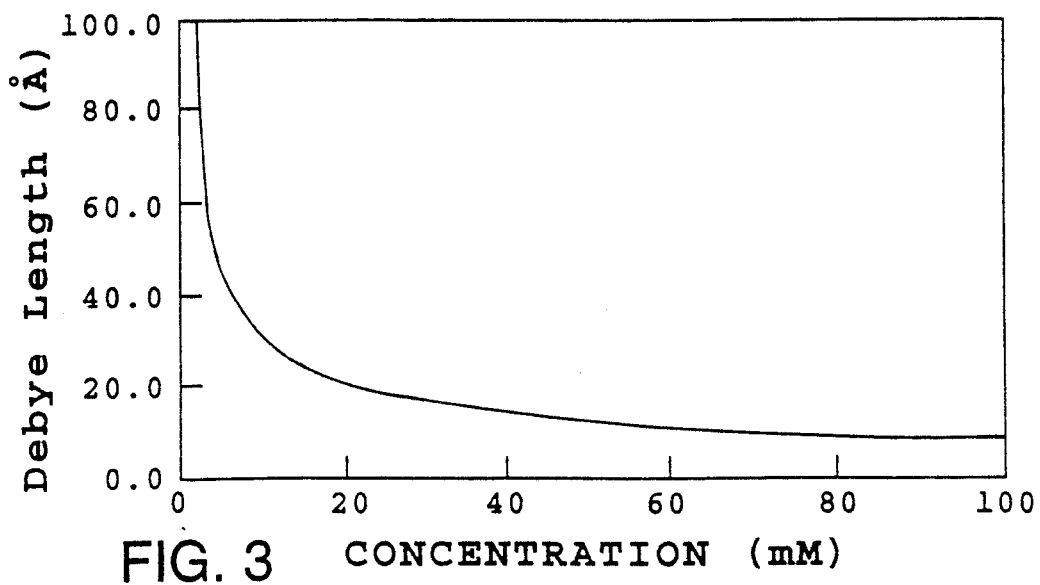
FIG. 3 illustrates the change in calculated Debye length as a function of univalent electrolyte for a charged particle.

The concept of an electrostatic liposome shell is analogous to Debye length, which corresponds roughly to the distance over which the electrostatic field of an ion exerts an appreciable effect. FIG. 3 shows a theoretical plot of Debye length as a function of concentration of a univalent electrolyte in solution. The rapid decrease in Debye length between 0-30 mM electrolyte closely mirrors the change in viscosity seen in FIG. 1 over the same electrolyte concentration range, and strongly suggests the the viscosity effect seen in the present invention is due to electrostatic shielding and "ordering" of liposomes in charged spherical shells.

From the foregoing, it can be appreciated how the composition can be formulated to achieve a desired viscosity. In particular, greater viscosity can be achieved by one or more of the following:

(a) Increasing the concentration of lipid in the composition. For example, from Table 1, it is seen that increasing the concentration of lipid from 100 μg/ml to 200 μg/ml reduces the thickness of the calculated "packing" spheres from 1,400 Å to about 700 Å. This much closer packing of the charged liposomes would produce substantially more overlap of the electrostatic-repulsion effects, tending to hold the liposomes in a more rigid (viscous) condition;

(b) Increasing the surface density of liposome surface charge. Greater charge density would increase the thickness of the electrostatic shells, and thus produce more rigid packing at any given lipid concentration; and (c) Decreasing the conductivity, i.e., ionic strength, of the aqueous medium. The strong dependence of Debye length (FIG. 3) and composition viscosity (FIG. 1) in the range 1-10 mM univalent electrolyte demonstrates the extreme sensitivity of the composition to low electrolyte concentrations.

F. Positively Charged Liposome Gel Composition

In another aspect, the invention includes a high-viscosity liposome gel composition for use either in applying lipid to a mucosal tissue, or in administering a liposome-entrapped drug to a mucosal surface tissue.

The composition includes a low-conductivity aqueous suspension medium having a selected pH between about 5.5 and 8.5, and between about 7-25 weight vesicle-forming lipids. The lipids contain between about 5-50 weight percent positively-charged vesicle-forming lipids, and (ii) the balance of neutral vesicle-forming lipids. Preferably the positively charged lipids are the type described above which include a spacer at least 3 atoms in length greater between the lipophilic moiety of the lipid and the positively charged polar head group. Such lipids provide enhanced liposome retention on mucosal surfaces, as detailed in U.S. Pat. No. 4,804,539. In particular, the positively charged lipid components in the composition preferably includes PE derivatives which are conjugated with basic amino acids, and/or amphiphilic benzylamine compounds, as described above. Lipid compositions 9-12 above are exemplary.

The compositions are formed substantially as described in Section D, where the aqueous hydration medium may either be a low-conductivity medium, or a medium containing a zwitterionic compound which allows pH titration to a low-conductivity medium. Example 4 illustrates a PC/BDSA gel composition formed by solvent injection.

In one embodiment, the gel composition is formulated as a lipid supplement for treatment of dry eye. Preferred lipid compositions are detailed in co-owned U.S. Pat. No. 4,818,537 for "Method of Treating Dry", and preferably include 10-40 mole percent benzlamine lipid, such as BDSA. The present composition differs from the earlier formulation in that high viscosity is produced by electrostatic effects rather than by high-viscosity polymers.

Alternatively, the positively charged liposome gel can be formulated to contain entrapped drug agents, for slow drug release from the liposomes.

II. Utility

The gel composition of the invention is useful as a moisturizing agent for application to dry or aging skin, and/or for applying cosmetic agents, such as vitamin A, UV-blocking agents, or retinoids, to the skin. The gel is easily delivered from a tube or the like, is relatively non-greasy to the touch, and is clear when applied to the skin. One unique property of the gel is its ability to dissolve or melt over time as the gel becomes infused with salts on the skin. Thus, the viscous gel may be applied to the skin in gel form, but become quite fluidic as it is rubbed into the skin.

The gel may also be used as a drug delivery composition, for delivering a liposome-entrapped drug transdermally. The drug to be administered is typically a lipophilic drug, such as an anti-inflammatory steroid drug, which is entrapped in the gel liposome lipids at a concentration between about 1-20 weight percent. It will be appreciated that a charged lipophilic drug may be administered, where the charge on the compound contributes to the liposome surface charge.

Because of its high viscosity, the gel composition is useful as a drug delivery vehicle for surgical wounds, where slow drug release over a several-hour to several-day period is desired. The use of the gel for long-term delivery of epidermal growth factor (EGF) in surgical wounds, including ophthalmic surgical applications, has been detailed in co-owned patent application for "EGF-/Liposome Gel Composition and Method", filed Feb. 24, 1989.

The gel composition of the invention also provides a number of advantages for lipid or drug administration to mucosal tissue. For treatment of dry eye, where the gel serves as a source of lipid and moisture, the gel has the advantage of optical clarity. Further, where the liposomes contain positively charge lipid components with charged-group spacers, as described above, the liposomes themselves have enhanced retention to corneal surfaces. The liposomes may also be used for drug delivery to the eye or other mucosal surfaces, with advantages of greater retention, i.e., less flow from, the site of application.

According to another important advantage, the gel composition of the invention combines high viscosity with low lipid concentration, so that the composition is relatively inexpensive in terms of materials cost. Further, additives, such as high molecular weight polymers, colloids and the like, are avoided.

The following examples are intended to illustrate various compositions, methods of preparations, and characteristics of the present invention. The examples are in no way intended to limit the scope of the invention.

EXAMPLE 1

Preparation of EPG Liposome Gel Composition

EPG was purchased from Avanti Polar Lipids (Birmingham, AL) and EPC was purchased from Asahi Chemical Company (Tokyo, Japan); cholesterol was from Croda, Inc. (New York, N.Y.); and α-tocopherol (Vitamin E) from Hoffman-La Roche (Nutley, N.J.). Aminoacetic acid (glycine) was from J. T. Baker (Philipsburg, N.J.).

Liposomes were prepared by thin film hydration of a dehydrated lipid mixture containing EPG/EPC/cholesterol/α-tocopherol (1/1/1/0.03, w/w/w/w). The lipids were dissolved in chloroform:methanol (2:1) and a total of 33 g of lipid were added to a round bottom flask and dried in vacuo to a thin film. To this film was added 267 ml of hydration buffer containing 2.3% (w/v) glycine, pH 6.0. Hydration was carried out for 1-2 hours with swirling. The gel material had a stiff, gel-like consistency.

The resulting liposome dispersion was injected by extrusion through a Gelman Acrodisc (0.2 μ pore size) into 1 or 10 ml plastipak syringes which were wrapped in aluminum foil and labeled. An aliquot of the liposome gel was set aside, and "collapsed" back into a lotion by the addition of concentrated saline, and served as a control.

Samples were assayed for total lipid phosphate, cholesterol content, pH, viscosity, osmolarity, particle size and pyrogen levels (Table 2). Mean diameters were assayed using the Nicomp laser particle sizer.

TABLE 2

| Characterization of Liposome Gel Compositions | | |
|---|---|---|
| Assay (units) | Control (collapsed Gel) | Gel |
| Total Lipid Phosphate (μmol/gm) | 87.0 | 87.0 |
| Cholesterol (mg/gm) | 34.3 | 32.2 |
| Buffer pH | 6.0 | 6.0 |
| Osmolarity (mOsm) | 319 | 305 |
| Viscosity (Cps) | 3,600 | 20,500 |
| Nicomp Mean Diameter (nm) | 644 | 666 |

EXAMPLE 2

Viscosity of the EPG Gel Liposome Composition

Five separate batches composed of EPG/EPC/cholesterol/α-tocopherol (1/1/1/0.03, w/w/w/w) liposomes were prepared as described in Example 1. The viscosity of each of the batches was determined (a) without addition of NaCl, and after addition of (b) 0.05%, (c) 0.1, and (d) 0.2% by weight NaCl. At each salt concentration, the mean viscosity of the compositions tested was determined. The measured values, expressed as extrapolated Cps at 1 per second shear rate, are shown in FIG. 1 and in Table 3 below.

Viscosity was determined using a Brookfield DV-II cone/plate viscometer. Viscosity readings were made at all relevant spindle speeds. Spindle speeds were converted to the shear rate. Plots of log (viscosity) versus log (shear rate) were prepared from which the viscosity at a shear rate of one reciprocal second was extrapolated.

TABLE 3

| % NaCl | Mean Viscosity (Extrapolated Cps at 1 sec. shear rate) |
|---|---|
| 0.0% | $13.3 \times 10^3$ |
| 0.05% | $2.7 \times 10^3$ |
| 0.1% | $1.5 \times 10^3$ |
| 0.2% | $0.8 \times 10^3$ |

The mean viscosity of the composition in the absence of NaCl corresponds to a stiff, gel-like consistency. As seen, addition of only a slight amount of salt reduces the viscosity several-fold, producing a thinner, lotion-like consistency.

EXAMPLE 3

Processing EPG Liposome Gel Composition

Liposomes were prepared by thin film hydration of a dehydrated lipid mixture containing EPG/EPC/cholesterol/α-tocopherol (1/1/1/0.03, w/w/w/w), as described in Example I, except that the hydration buffer used to produce the liposomes contained 50 mM glycine, adjusted to pH 8. The liposome suspension was highly fluidic.

The suspension was sized by extruding multiple times through a 0.2 micron polycarbonate membrane. The sized liposomes were then sterilized by filtration through a 0.22 micron depth filter. To this sterilized material was added 1/5 volume of sterilized 5X glycine buffer (12% glycine by weight, pH 6.0). The final suspension had a stiff, gel-like consistency.

EXAMPLE 4

Positively Charged Liposome Gel Composition

Fully hydrogenated soy PC (HSPC) was obtained from American Lecithin Company (Atlanta, Ga). Benzyldimethylstearylammonium chloride (BDSA) was obtained from Aldrich Chemical Company (milwaukee, Wis.).

A lipid mixture containing 32 g HSPC and 4 g BDSA was dissolved in 38 ml ethanol, at about 60° C. This lipid solution was then injected slowly, with stirring, into 500 ml of distilled water, also at 60° C. The liposome suspension which was produced was cooled to room temperature, resulting in a viscous substantially non-flowing gel.

Although the invention has been described with respect to particular embodiments, methods, and applications, it will be apparent that various changes and modifications can be made without departing from the invention .

It is claimed:

1. A liposome gel composition comprising
   (a) an aqueous suspension-medium, whose conductivity is no more than that of a fully ionized univalent electrolyte whose concentration is between about 5–10 mM, having a selected pH between about 3.5 and 10.5, and
   (b) suspended in the medium, at a concentration of between about 7 to 25 weight percent total lipid, liposomes composed of (i) at least about 5 weight percent changed vesicle-forming lipids which contribute a common net change to the outer surfaces of the liposomes, at the selected pH, and (ii) the balance of neutral vesicle-forming lipids.

2. The gel composition of claim 1, wherein the aqueous medium contains a zwitterionic compound whose isoelectric point is substantially at the selected pH.

3. The gel composition of claim 2, wherein the zwitterionic compound is a neutral amino acid, and the selected pH is between about 5.5 and 8.5.

4. The composition of claim 3, wherein the concentration of zwitterionic compound is such as to produce a substantially isotonic medium.

5. The composition of claim 1, wherein the charged vesicle-forming lipids include phosphatidylglycerol, and the neutral vesicle-forming lipids include phosphatidylcholine.

6. The composition of claim 5, wherein the liposomes are composed of between 20–40 weight percent each of phosphatidylglycerol, phosphatidylcholine, and cholesterol.

7. The composition of claim 1, for use in applying liposomes to a mucosal tissue, wherein the charged vesicle-forming lipids are positively-charged lipids.

8. The composition of claim 7, wherein the charged lipids include a phosphatidylethanolamine conjugate prepared by derivatizing phosphatidylethanolamine with a basic amino acid.

9. The composition of claim 7, wherein the charged lipids include a benzylamine lipid.

10. A liposome gel composition comprising
    (a) an aqueous suspension medium, whose conductivity is no more than that of a fully ionized univalent electrolyte whose concentration is between about 5–10 mM, having a selected pH between about 3.5 and 10.5, and containing a zwitterionic compound whose isoelectronic point is substantially at the selected pH, and
    (b) suspended in the medium, at a concentration of between about 7–20 weight percent total lipid, liposomes which are composed of (i) at least about 5 weight percent charged vesicle-forming lipids which contribute a common net charge to the outer surfaces of the liposomes, at the selected pH, and (ii) the balance of neutral vesicle-forming lipids.

11. The gel composition of claim 10, wherein the total lipid concentration of liposome lipids is substantially between about 8–15 weight percent.

12. The gel composition of claim 10, wherein the zwitterionic compound is a neutral amino acid, and the selected pH is between 5.5 and 8.5.

13. The composition of claim 10, wherein the concentration of zwitterionic compound is such as to produce a substantially isotonic medium.

14. The composition of claim 10, wherein the charged vesicle-forming lipids include phosphatidylglycerol, and the neutral vesicle-forming lipids include phosphatidylcholine.

15. The composition of claim 14, wherein the liposomes are composed of between 20–40 weight percent each of phosphatidylglycerol, phosphatidylcholine, and cholesterol.

16. The composition of claim 10, for use in applying liposomes to a mucosal tissue, wherein the charged vesicleforming lipids are positively-charged components.

17. The composition of claim 16, wherein the charged lipids includes a phosphatidylethanolamine conjugate prepared by derivatizing phosphatidylethanolamine with a basic amino acid.

18. The composition of claim 16, wherein the charged lipids includes a benzylamine lipid.

19. A liposome gel composition for use in applying liposomes to mucosal tissue comprising
    (a) an aqueous suspension medium, whose conductivity is no more than that of a fully ionized univalent electrolyte whose concentration is between about 5–10 mM, having a selected pH between about 3.5 and 10.5, and
    (b) suspended in the medium, at a concentration of between about 7–25 weight percent total lipid, liposomes which contain at least about 5 weight percent positively-charged vesicle-forming lipids, and the balance of neutral vesicle-forming lipids.

20. The gel composition of claim 19, wherein the aqueous medium contains a zwitterionic compound whose isoelectric point is substantially at the selected pH.

21. The gel composition of claim 20, wherein the zwitterionic compound is a neutral amino acid, and the selected pH is between about 5.5 and 8.5.

22. The composition of claim 20, wherein the concentration of zwitterionic compound is such as to produce a substantially isotonic medium.

23. The composition of claim 19, wherein the charged lipids includes a phosphatidylethanolamine conjugate prepared by derivatizing phosphatidylethanolamine with a basic amino acid.

24. The composition of claim 19, wherein the charged lipids includes a benzylamine lipid.

25. The composition of claim 24, for use in treating dry eye, wherein the composition includes between about 10–40 mole percent BDSA.

26. The composition of claim 19, for administering a lipophilic agent to the eye, wherein the agent is associated with the lipid phase of the liposomes in the composition.

27. A method of preparing a liposome gel composition comprising
    mixing a lipid composition containing at least about 5 weight percent charged vesicle-forming lipids having a common charge at a selected pH between about 3.5 and 10.5, and the balance of neutral vesicle-forming lipids with an aqueous suspension medium whose conductivity is no more than that of a fully ionized univalent electrolyte whose concentration is between about 5–10 mM, at a total lipid concentration of between about 7–25 weight percent.

28. The method of claim 27, wherein the aqueous medium contains a zwitterionic compound whose isoelectric point is between about pH 5.5 and 8.5.

29. The method of claim 28, wherein said mixing includes adding the lipid composition to an aqueous medium whose pH is substantially different from the isoelectric point of the zwitterionic compound, thereby to form a fluid non-gel liposome suspension, and adjusting the pH of the suspension to the isoelectric point of the zwitterionic compound, to produce the desired gel suspension.

30. The method of claim 29, which further includes processing the fluid non-gel liposome suspension to achieve a desired liposome size change prior to said adjusting.

31. The method of claim 29, which further includes processing the fluid non-gel liposome suspension to remove non-liposome-bound solutes from the suspension prior to said adjusting.

32. The method of claim 28, wherein the zwitterionic compound is a neutral amino acid.

33. The method of claim 28, wherein the concentration is such as to produce a substantially isotonic gel suspension.

* * * * *